350-167
6/16/81    XR    4,273,443    SR

United States Patent [19]

Hogg

[11] 4,273,443
[45] Jun. 16, 1981

[54] METHOD AND APPARATUS FOR MEASUREMENT OF RERADIATION IN PARTICLE FLOW CELL SYSTEMS

[75] Inventor: Walter R. Hogg, South Miami, Fla.

[73] Assignee: Coulter Electronics, Inc., Hialeah, Fla.

[21] Appl. No.: 93,311

[22] Filed: Nov. 21, 1979

[51] Int. Cl.³ .................. G01N 21/49; G01N 21/85; G02B 27/12
[52] U.S. Cl. ................................ 356/343; 250/574; 350/167; 350/169
[58] Field of Search ............................. 356/336–338, 356/ 343, 39, 71; 250/574; 350/167, 169, 162 SF

[56] References Cited

U.S. PATENT DOCUMENTS

| 3,705,771 | 12/1972 | Friedman et al. | 356/39 |
| 4,050,782 | 9/1977 | Uchida et al. | 350/211 X |
| 4,072,421 | 2/1978 | Coyne et al. | 356/338 X |

OTHER PUBLICATIONS

Mix, A. L. Jr., "Single Lamp Matrix Illuminator", IBM Tech Disclosure Bulletin, vol. 12, No. 4, Sep. 1969, p. 522.

*Primary Examiner*—John K. Corbin
*Assistant Examiner*—Bruce Y. Arnold
*Attorney, Agent, or Firm*—Silverman, Cass & Singer, Ltd.

[57] ABSTRACT

Measurement of the energy and direction of radiation, typically scattered light, produced by particles passing through an optical sensing zone is improved in focusing of the scattered light and flexibility in the choice of focal length for positioning of photoresponsive devices.

The improvement is obtained by collimating the collected scattered light entering a deviating device, typically a fresnel prism, and then focusing the emerging separate, independent beams for measurement.

Collimation can be obtained using optical elements including lens systems or reflective systems such as those employing parabolic reflection.

32 Claims, 8 Drawing Figures

METHOD AND APPARATUS FOR MEASUREMENT OF RERADIATION IN PARTICLE FLOW CELL SYSTEMS

CROSS REFERENCE TO RELATED APPLICATIONS

Each of the following copending patent applications filed in the names Walter R. Hogg and Albert Brunsting is specifically incorporated herein by reference:

"Apparatus and Method for Measuring the Distribution of Radiant Energy Produced in Particle Investigation Systems", Ser. No. 000,439, filed Jan. 2, 1979; "Apparatus and Method for Measuring Scattering of Light in Particle Detection Systems", Ser. No. 000,438, filed Jan. 2, 1979; and "Radiant Energy Reradiating Flow Cell System and Method", Ser. No. 20,817, filed Mar. 15, 1979.

BACKGROUND OF THE INVENTION

This invention is concerned generally with improved measurement of radiant energy distribution such as that of scattered light and more particularly is concerned with the measurement of the energy and direction of light produced and distributed by particles passing through an optical sensing zone whereby to enable the identification of the particles and/or their characteristics. The invention will be discussed in connection with light scattering but is not limited thereto.

The invention herein has relatively wide application but particularly is of value in the identification of white blood cells, cancer cells and other biological particles.

There is a considerable body of literature and prior art on the work which has been done by others in the identification of biological cells and it would be of some value to review the same briefly. It would be advantageous also to delineate the relationship of this invention with the apparatus which has been utilized and is described in the prior art.

Basically, a sensing zone is established by directing a beam of concentrated light to a small volume through which the particles are to be passed, the particles are directed to pass through the zone and the reradiated light (scattered or fluorescent) is detected in different geometric locations around the zone. Scattering may occur backward or forward of the zone relative to the light source.

In its simplest form, a stream of liquid or air carrying the particles is flowed through a pipe and at a transparent location along the pipe a beam of light is projected across the stream. A photodetector on the side of the pipe opposite the source of the beam of light will detect a change in its response each time that a particle passes. Obviously the fact of change enables the particles to be counted. The "shadow" thrown by the particle on the photodetecting device provides some information as to size. Other photodetecting devices can be positioned at locations spaced from the axis of the light beam to give signals which are related to the amount of light scatter in different polar locations.

In biological cells, the condition of the interior of the cell will produce scattering of light in different ways and many of the apparatuses of the prior art are concerned with the method and techniques whereby the effects of light scattering help identify the cells.

Identification of the cells, especially white blood cells, is needed for diagnosis and detection of disease, for the ascertaining of patient condition and the effects of therapy, etc. Present methods and apparatus for this purpose are channeled toward the automation of the identification techniques to enable high speed measurements and positive identification. This is to enable the elimination of the slow, tedious and inaccurate manual methods and have been classically practiced in laboratories, clinics and hospitals.

The systems and apparatus which are known utilize a fluid flow which tends to pass the particles to be measured through a sensing zone one by one. Although the fluid may be a gas, generally in the study of biological particles this is a liquid such as a saline solution whose purpose importantly is to preserve the integrity and the condition of the particles. Gas and air as fluids for transporting particles to and through sensing zones are used more commonly in the study of industrial particles such as fly ash, dust, comminuted minerals etc.

Considering principally biological particles (although the prior art to be mentioned is not necessarily limited thereto) typically such particles are entrained in a sheath of liquid which is either circular or almost planar in cross section at the sensing zone. Several U.S. patents which disclose this type of entrainment and sensing zone are: U.S. Pat No. Re. 29,141; U.S. Pat. Nos. 3,413,464; 3,657,537; 3,705,771; 3,785,735 and 3,791,196.

After the particle passes into the sensing zone, the light or other radiant energy which has been directed at the sensing zone by some means such as a concentrated lamp beam or a laser is measured at different locations relative to the sensing zone. Typical of these devices are several of those mentioned above as well as in U.S. Pat. No. 3,835,315. Systems for such measurements are disclosed in U.S. Pat. Nos. 4,070,113 and 4,150,360.

The problem of measuring the scattered light at different locations has been attacked by others but three important disadvantages have been difficult to overcome. The first is the disadvantage of not being able to get enough information because of the difficulty of measuring a plurality of points. The second is the disadvantage of complex and difficult to manufacture apparatus with its attendant companion disadvantage of great expense. The third is the disadvantage of not getting enough energy from the scattered light at all measuring points to give meaningful data.

Each of the four prior art references mentioned hereinafter has one or more of these disadvantages.

The oldest of these references is U.K Pat. No. 137,637 of 1920 to Pollard which utilizes expensive conical frustums and reflecting prisms. The scattered light is viewed by a microscope and/or measured by crude means compared to those available at the present time.

The second of these references is Frommer U.S. Pat. No. 3,248,551 which utilizes a compound type of annular reflector that has two surfaces and concentrates the scattered light captured by the respective surfaces and reflects same to separate photomultiplier tubes. It is quite obvious from an examination of this patent that the two-surface reflecting device is most difficult and complicated to manufacture; hence one which would require collection from many more than just two angles or polar regions would be even more difficult and expensive to manufacture. In this structure, the collection and deviation of the scattered radiant energy is effected by a single element.

Both the Pollard and the Frommer patents utilize only reflection for concentrating the scattered light thereby not having the simplicity and efficiency of the invention. The number of regions of light scatter from which information can be obtained is severely limited in these prior art devices.

The third and fourth of these references comprise two publications describing a device which is mentioned in U.S. Pat. No. 4,070,113 and more fully disclosed in U.S. Pat. No. 3,689,772 as a type of photovoltaic detector which has concentric rings formed on a disc that is several inches in diameter. The light from the scattering zone is permitted to fall directly onto this detector which then provides electrical signals related to the energy of the light at different distances from the center of the beam. The publications are an article entitled "Light-Scattering Patterns of Isolated Oligodendroglia" by R. A. Meyer, et al in *The Journal of Histochemistry and Cytochemistry*, Vol. 22, No. 7 pp 594–597, 1974 and a second article entitled "Gynecologic Specimen Analysis by Multiangle Light Scattering in a Flow System" by G. C. Salzman et al in the same journal, Vol. 24, No.1, pp. 308–314, 1976. In the articles reference is made to the same or a similar detector device which is identified as a Recognition Systems, Inc. detector.

The ring detector which has been described above is quite expensive at the present time. It typically comprises 64 photodiodes arranged in rings and wedges, all on the same substrate. If any element or increment of the detector fails or is damaged it may be necessary to discard the entire device. Additionally, the contacts for the diodes are brought out to a narrow edge segment at which point they are required to be connected into electrical circuitry. This is a delicate and precise operation not easily effected by unskilled technicians.

Additionally the inner rings are very small while the outer rings are quite large. Thus the radiant energy is weakly diffused over the outer rings giving low power density. Detection requires amplification with decrease of signal to noise ratio. Additionally, the electrical capacitance of the outer rings is substantially high which results in loading and deterioration of signal. This is a problem where the particles which move through the sensing zone at high speed generate light pulses which may be as short as several microseconds.

Copending application Ser. No. 000,439 discloses a method and apparatus which eliminates the disadvantages of the prior art through the use of a light deviating device constructed from prismatic elements forming a fresnel lens which receives the scattered light from the sensing zone and effects a division of the scattering energy from a large region into increments which represent respective different areas or angles of scatter. This is done by transmitting the scattered light through the lens to achieve independent concentrated beams in an amount equal to the number of elements forming the lens, directing and focussing the resulting independent beams on respective independent photoconductive devices or upon incremental areas of a large photoresponsive device capable of giving independently indentifiable signals, for example a television camera element.

The independent photoconductive devices are located in any convenient array, are conventional in construction and hence are highly economical and easily replaced independently. The capacitance to ground is low permitting rapid voltage change and good response, thereby preserving the amplitude of electrical signals resulting from the high speed passage of particles. The processing of large numbers of signals is thus rendered easier in relatively simple electric circuitry than if the signals were not clearly defined.

The invention permits of considerable latitude in configuration, placement, construction and arrangement thereby providing high flexibility for almost any kind of system, but also with no loss in convenience and economy of use.

I have now found that improved focusing and flexibility in the choice of focal length and positioning of the photoresponsive devices can be obtained by collimating the collected scattered light entering the prismatic elements of the fresnel lens deviating device and then focusing the emerging separated, independent beams for measurement. As a result, the variation in the angles of deviation or "smearing" produced by an individual prismatic element of the fresnel deviator can be eliminated, without requiring thinner prism elements, and consequently focusing can be made more precisely.

The word "confluence" is used herein as a noun according to its normal use and additionally as a verb to signify the tapered directing of a cone of radiant energy toward its apex or focus.

SUMMARY OF THE INVENTION

An improved method and apparatus are disclosed for measuring the distribution of radiant energy produced in particle investigation systems such as light scattering systems.

Sensing zone is established by directing a beam of radiant energy such as visible light to the zone and passing particles through the zone preferably in such a manner that they traverse it essentially one-by-one.

Collimation of collected characteristically scattered light, reradiated from the particle disturbed beam, permits increased accuracy in prismatic partition and convergence of the partitioned light at separate locations for photoresponsive measurements of angular distribution.

Suitable collimation can be achieved by optical elements including lens systems or reflective systems such as the use of parabolic reflection of scattering at a sensing zone located at the parabolic focal point.

DESCRIPTION OF THE PREFERRED EMBODIMENTS

The invention is believed to provide a greater quantity and more accurate scattering data than known methods and apparatus as a result of which it is useful for the establishment of information related to specific types of particles by passing known particles into the sensing zone in order to learn the scattering effects of such particles for use in other work where unknown particles are being identified.

Figure 1:
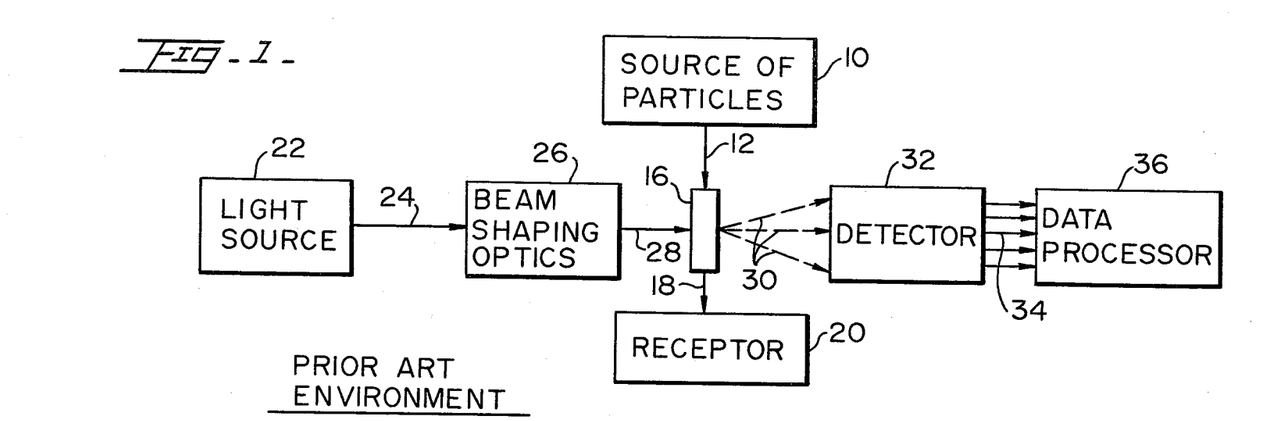
FIG. 1 is a diagrammatic view of the prior art environment in which the invention is utilized.

FIG. 1 illustrates a prior art system disclosed in U.S. Pat. No. 4,070,113 which shows the environment in which this invention is utilized. Here a source of particles 10 is provided which may feed, for example, white blood cells, exfoliated cells or the like in a diluent by way of the path 12 to the flow-through element 16. This may be effected in this simple flow or with some additional second diluent which produces a particular form of geometric cross section of fluid in a sensing zone. The additional diluent may comprise a stream of liquid under pressure surrounding the main flow to produce sheath flow conditions through the body of the liquid whereby to confine the particle stream. The basis stream itself may form a flat planar stream through the sensing zone.

From the flow-through element 16, the fluid that has been passed through moves along the path 18 to a suitable receptor 20 which may be waste, another system or an accumulator.

The source of radiant energy is here shown as a laser 22 but can be any suitable source of light or the like. The invention provides an efficiency which enables the laser used to be of low power with a minimum of heat generation. The resulting beam is passed along the optical axis 24 to an optical system or train represented by the lens 26 which shapes and focusses the incident radiant energy onto the sensing zone of the flow-through element 16, the emergent light being scattered and providing a plurality of radiating beams indicated at 30. Only three such beams are shown as representative, there being a continuous spread of the energy, the amount of radiant energy at any diverging angle and in any sector being dependent upon the size, shape, orientation and morphology of the scatterer (particle) plus characteristics of the incident light. A detector 32 is provided which is ideally constructed to respond differently at its different geometric aspects facing the beams 30 so that at incremental locations over the area of its frontal aspect it will produce different identifiable signals, notably, signals of different intensities. These signals are passed through the channels 34 to some form of data processor 36. From the signals and their relationship to one another, both as to intensity and geometric location, the particle which produced the signals may be identified or at least characterized.

Figure 2:
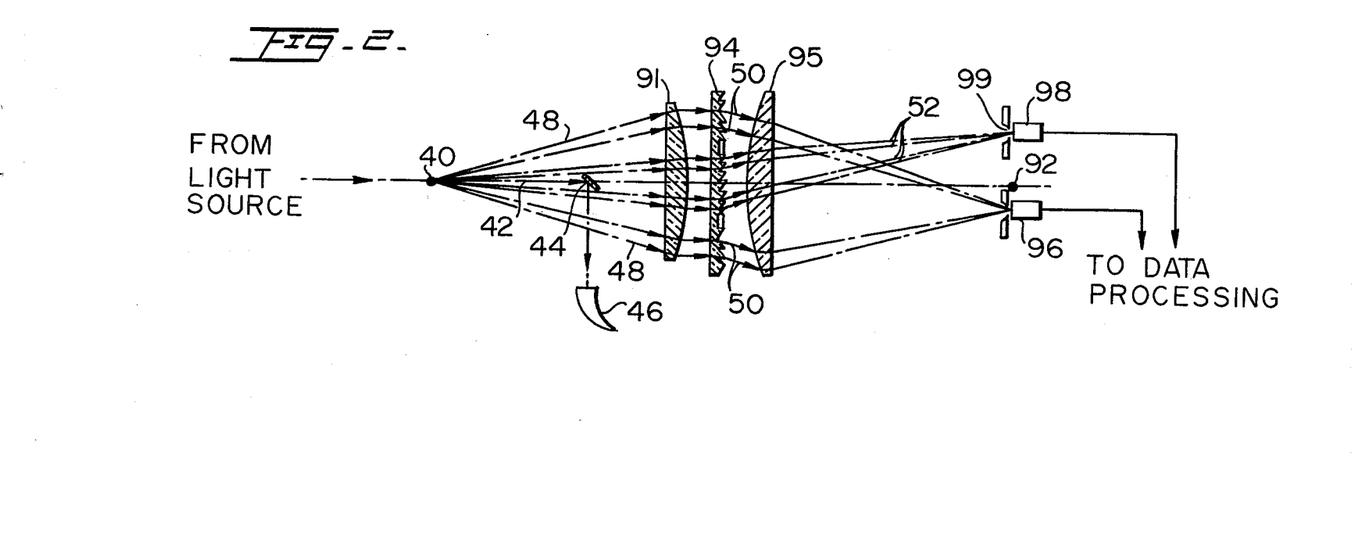
FIG. 2 is a diagrammatic generally sectional view through a simplified form of the invention showing the manner in which the scattered light from the sensing zone is collected, collimated and thereafter deviated and focused toward the photoresponsive devices.

A simplified embodiment of this invention is illustrated in FIG. 2. The point 40 represents the location of what may be termed the scattering point, this being, for example, a sensing zone through which particles are flowed. Although not here illustrated, it may be assumed that these particles enter the sensing zone laterally of the optical axis 42 and cross the axis at said point 40 one at a time. Light or other radiant energy from a source such as a laser is directed from the left in the view toward the scattering point 40 along the optical axis 42 with the central or main portion of the beam being captured by an axially located angled mirror 44 directing the central portion of the beam to a laterally located absorbing device 46 which is known in the art as a light dump.

The scattered rays of radiant energy from the scattering point 40 are concentrated or collected and collimated by a collimating lens 91 positioned so that its first focal point is coincident with the sensing zone 40 thereby refracting the entering scattered rays, represented at 48, substantially to collimate the emerging rays. While collimating lens 91 is shown as a typical plano-convex thin lens, any suitable substantially collimating lens system can be employed.

Figure 2A:
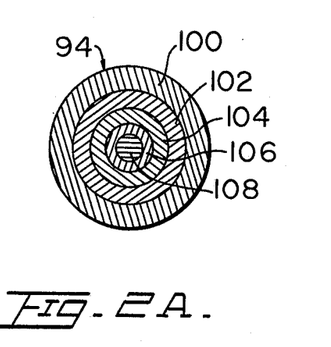
FIG. 2A is a front-on elevational view of the fresnelled lens assembly of FIG. 2 showing one form thereof and FIG. 2B is the same but showing another form thereof.
Figure 2B:
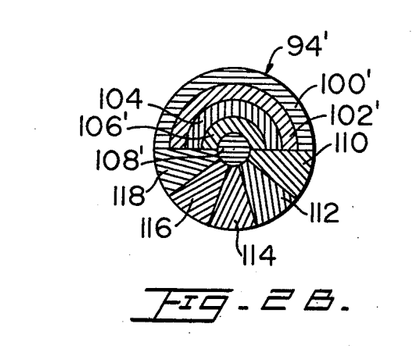
Figure 2C:
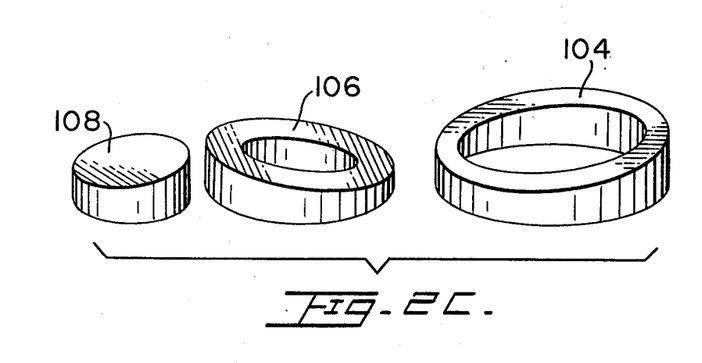
FIG. 2C is a perspective view of several cylinders which can be assembled to produce a non-fresnelled equivalent, especially useful for very small embodiments, of deviator prisms of the type shown in FIG. 2.

The collimated pattern of parallel rays from lens 91 enter a fresnel prismatic deviator 94 formed by five annular prisms constructed as shown in FIG. 2A or 2C, and more fully described in copending application Ser. No. 000,439. Fresnel deviator 94 functions to separate different annular portions of the collimated pattern of parallel rays into five annular ray groups; within a given annular ray group 50 the rays remain substantially parallel. However, the different ray groups are deviated to project in different directions. As indicated in FIG. 2, annular ray group 50 is shown being deviated in a direction different from a second annular ray group 52.

Focusing lens 95 accurately focusses each of the different ray groups including 50 and 52 at a corresponding different point location for representative photodetectors 96 and 98. Pinholes 99 can be employed at each sharp focal point to attenuate extraneous radiation and improve signal to noise ratio. Focusing lens 95 can be chosen for any desired focal length usually for spacing and placement of the photodetectors in a convenient focal plane. The focusing lens or suitable focusing lens system is consequently variable in focal length and easily modified such as for use with a conventional television vidicon for photodetection. In an embodiment not shown, a fresnel deviator and a focusing lens can be integrated into a single optical device.

An advantage of the arrangement in FIG. 2 is that the photodetectors can be standard photocells which are readily available. The radiant energy from the different elements of deviator 94 is focused on these photocells which may now be quite small and hence provide a better signal-to-noise ratio, lower capacitance in the circuits used and reduced costs. Replacement of defective or damaged photocells is readily effected without discarding a substantial and expensive part of the apparatus.

Only two sets of rays 50 and 52 are shown in FIG. 2 along with their companion photodetectors 96 and 98 but it should be understood that there will be a separate photocell for each prism element of deviator 94.

In FIG. 2A there is illustrated deviator 94 showing concentric annular fresnelled prisms 100, 102, 104, 106 and 108, all rotated about the central axis with respect to one another so that the prisms are at different angles. The number of prisms here shown is five for convenience, but any suitable other number could be used. It is understood that their respective analogs are five conventional prisms three of which may be as illustrated in FIG. 2C. The ridges due to the sawtooth cross sections of the various parts are indicated by cross hatching. Radiant energy is deviated by an angle which depends upon the slope of the ridge surfaces and in directions perpendicular respectively to these ridges. The collimated radiant energy captured in this case will form in effect five annular groups of parallel rays of which the groups 50 and 52 comprise those provided by the outer two annular prisms 100 and 102, respectively. Generally for the identification and study of biological particles the prismatic elements of the deviator 94 will be symmetrical about the center of the deviator 94.

In FIG. 2B an arrangement of elements composing the assembly 94' is illustrated in which the upper half of the element 94' is made out of annular fresnel prisms similar to those of FIG. 2A but only half of each annular prism element is used. Using only half is usually acceptable because of the normally symmetrical configuration of scatter patterns. Thus, there are four such semi-annular prismatic elements 100', 102', 104' and 106'. The center element 108' may be cylindrical for convenience of construction. In addition there are wedge shaped prismatic elements 110, 112, 114, 116 and 118 which collect rays of a different geometric area than annular. In this case the wedge shaped prismatic elements may be used to identify the presence of elongate constituents in certain particles. There will be a separate photodetector for each of the wedge shaped prismatic elements 110 to 118.

In the use of the apparatus, the electrical signals from the photodetectors 96 and 98 as well as all of the others which are not illustrated will be channeled to a suitable electrical system where the data will be processed. The analog signals may first be converted into digital if needed for the processing. For example, a computer may have a series of characteristics identified in its memory against which the signals are compared to ascertain the identification of the particle which caused the scattering. Scattering could have been caused by different kinds of structures and/or constituents within the particle, as for example, the organelles and their different densities, configurations and numbers.

Figure 3:
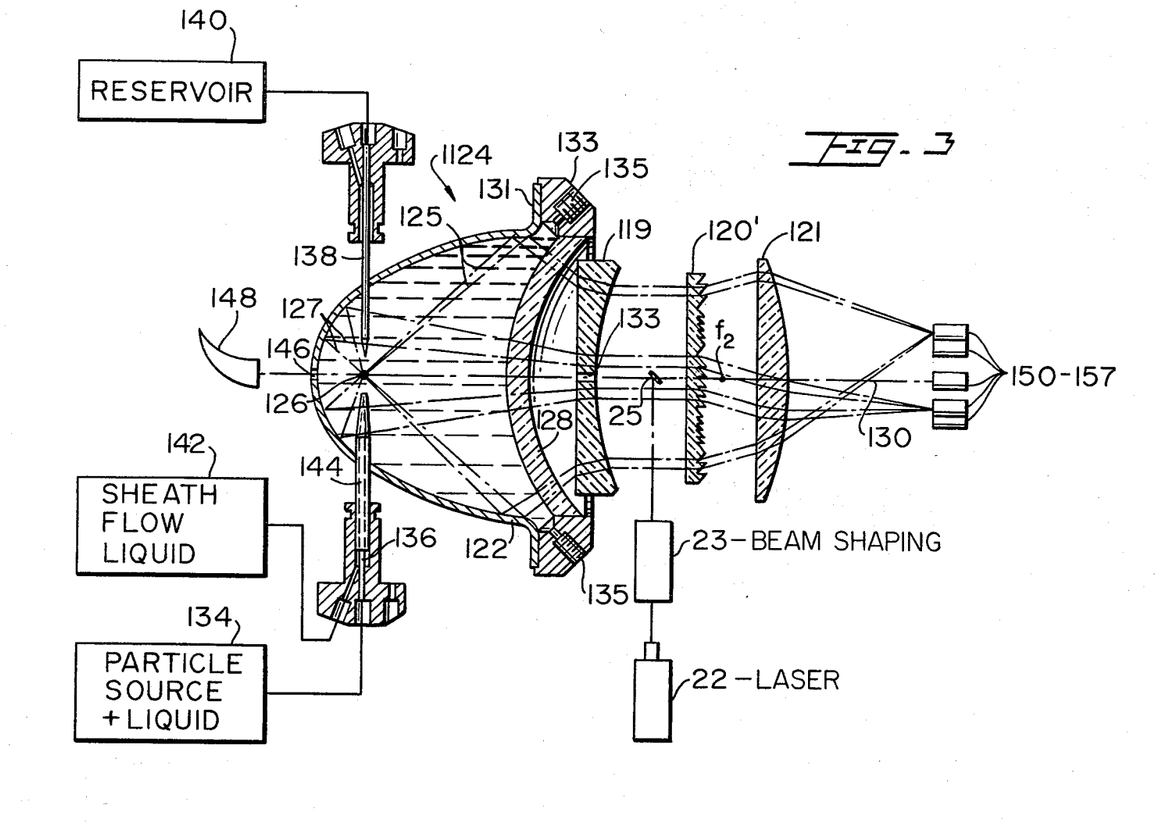
FIG. 3 is a diagrammatic generally sectional view through one form of the apparatus of the invention in which an ellipsoidal reflecting device is used to collect the radiant energy which is then collimated and directed to a fresnelled lens for deviation.

In FIG. 3 there is illustrated a form of the invention which utilizes a collimating lens 119 and refocusing lens 121 in addition to a fresnel deviator 120' and ellipsoidal reflector 122. The apparatus is generally designated by the reference numeral 1124. The sensing zone 126 in this case is located coincident with the interior left focal point of the reflector 122 which, as will be explained, is filled with diluent 123 of the same index of refraction as that which carries the particles.

The advantage of the addition of an ellipsoidal reflector as used here is that since the reflector 122 surrounds the sensing zone 126, it can capture the scattered light for a polar scattering angle which occurs in the vicinity of 0° to about 140°, depending on the eccentricity of the ellipse, as well as in all azimuthal angles. (In FIG. 3 the polar angles lie in the plane of the paper and the azimuthal angles lie in a plane perpendicular to the paper.) Back scattered light becomes increasingly important as the size of the particles to be measured decreases. For example, white cells and other biological cells may be of the order of 10 to 15 microns in diameter and their internal structure will normally be that which gives rise to the wider angles of scattering may have radii of curvature of the order of one micron and less.

In FIG. 3 the ellipsoidal reflector 122 has its forward opening closed off by a spherical transparent closure 128 that does not affect the direction of the collected radiant energy as it leaves the reflector 122. This closure has as its center of curvature the converging right hand focus f2 of the ellipsoid. Radiant energy originating in the laser 22 is shaped by conventional beam shaping optics 23 and directed by reflector 25 (or beam splitter not shown) to pass along the axis 130 through an opening 133 in the collimating lens 119 described hereafter, to the sensing zone or scattering point 126. The particle source 134 pumps the particles in the diluent liquid into a central conduit 136 into the interior of the ellipsoid 122 where it passes through the sensing zone 126 and into the discharge pipe 138 to a suitable reservoir 140 outside of the ellipsoid. In the meantime a source of third liquid 142 injects diluent through the concentric pipe 144 surrounding the conduit 136 so that there is a sheath flow confining the particles to the sensing zone 126.

The laser beam passes through the sensing zone 126, out through a transparent light port 146 in the rear of the ellipsoid and to a light beam dump 148 outside of the ellipsoid. The radiated energy from the sensing zone including representative forward scattered rays 127 and back scattered rays 125 with respect to the incident laser beam, as well as fluorescent energy, is reflected in the direction of the converging second or right focal point f2 of the ellipsoid.

Collimating lens 119 is positioned so that its focal point is coincident with the second or converging focal point f2 of the ellipsoid 122 in order that the reflected rays including rays 125 and 127 from the ellipsoid are intercepted incident on collimating lens 119 and emerge parallel to all other refracted rays from the ellipsoid. The collimated pattern of parallel rays enters fresnel deviator 120 constructed in a form similar to deviator 94 in FIG. 2, but having eight annular prismatic elements. The emerging eight deviated annular ray groups, of which two are shown produced in part by original reflected rays 125 and 127, are focused by refocusing lens 121 onto separate photodetectors 150-157 arranged circularly about axis 130.

While other collimating lens systems can be employed, collimating lens 119 is shown as a typical plano-concave negative lens which is preferably thicker at the periphery than at the optical axis 130.

In this case as in others described, the angle of deviation of the basic prism together with the focal length of refocusing lens 121 determine the radius of the ring defining the proper placement of the photo-detectors at points of beam focus.

The construction of the apparatus 1124 which is illustrated is not intended as limiting. In FIG. 3 the ellipsoidal reflector 122 has a rim flange 131 to which is attached a bezel 133. The bezel carries the spherical transparent closure 128 and can carry collimating lens 119 as well as the fresnel deviator 120'. The plugged openings 135 enable drainage and bubble removal.

Looking for the moment at the apparatus of FIG. 2, it should be appreciated that the laser being on the left and the light collecting occurring on the right, the only radiant energy being measured is that of the forward reradiation. In the case of the apparatus 1124 of FIG. 3, the laser 22 is on the right, the radiant energy which is represented by the beams 125 being typical of the back reradiation and being directed to one of the photocells. The radiant energy which is represented by the beams 127 reflected from the portion of the ellipsoid 122 to the left of the sensing zone 126 is typical of the forward scattered light and is directed to another of the photocells.

The apparatus 1124 of FIG. 3 will produce greater information than the apparatus of FIG. 2 because the ellipsoidal surface as shown will capture all scattered light from about half a degree to about 140°. Collimation of the reflected beams will prevent smearing and produce sharp focus at the photocells even when the annular prismatic elements of fresnel deviator 120 are large in radial width.

The structure of FIG. 3 may have several practical disadvantages. If the radial thicknesses or widths of the annular prisms of deviator 120 are very small fabrication may present problems. Another disadvantage is that commercially available ellipsoidal mirrors generally have an access hole at the closed end which is quite large.

Figure 4:
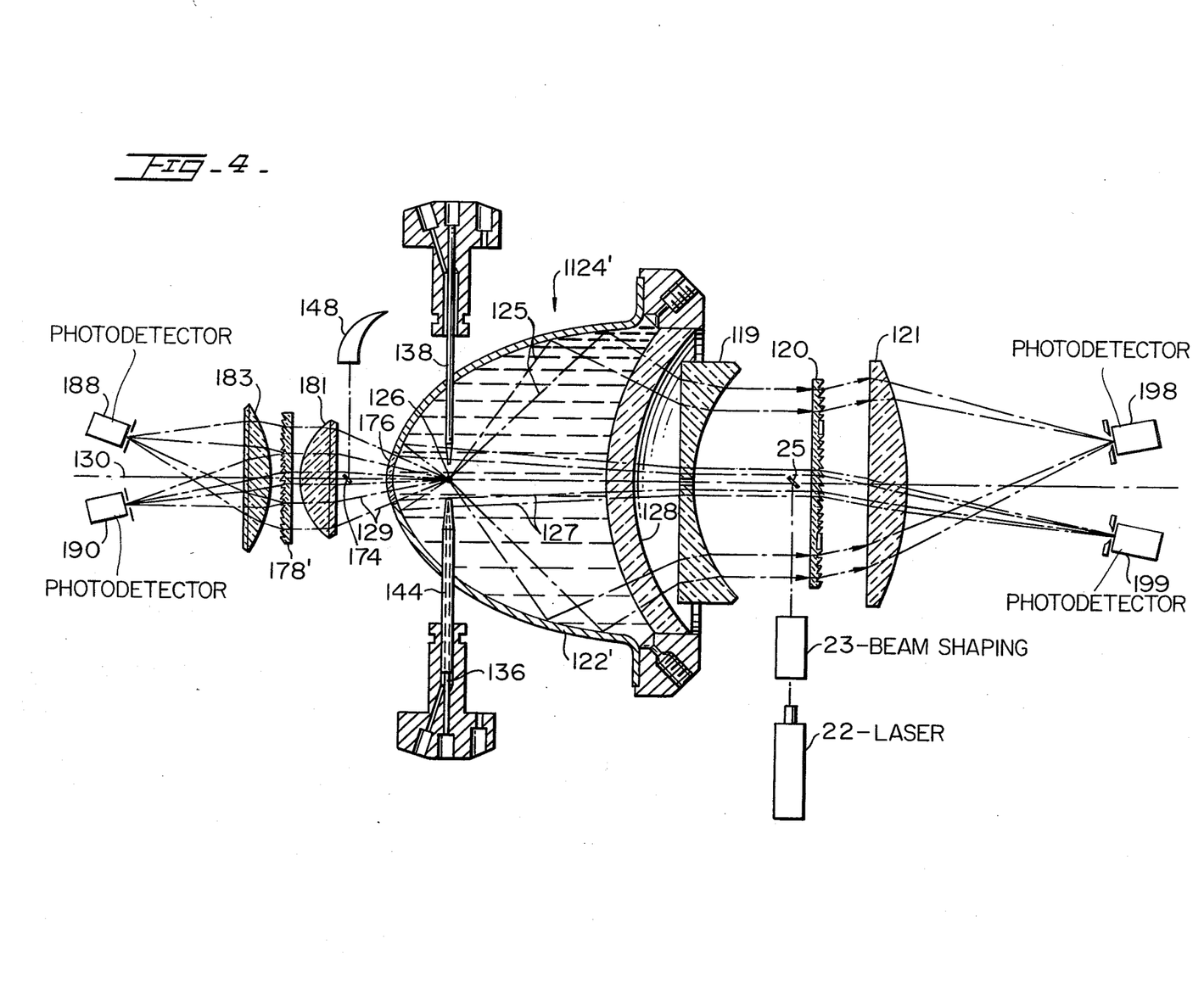
FIG. 4 is a view similar to that of FIG. 3 but illustrating another form of the invention in which narrow angle forward scattering measurements can be made.

According to the invention, in the device which is illustrated in FIG. 4, these problems to a large extent solve one another.

In FIG. 4 there is illustrated a system 1124' which takes advantage of the large opening in the commercially available ellipsoidal reflectors for collecting forward scattered light. The reference characters are generally the same as in FIG. 3. The ellipsoid 122' has the same means for forming the sensing zone and the same type of fresnel deviator 120. The light dump 148 is off to one side of the axis 130 and the center beam is directed there by a small reflector 174. The ellipsoid is drawn approximately full size. The ellipsoid 122' has the typical large hole 176 which is covered by a transparent spherical window centered on the sensing zone that will not adversely affect the operation of the device.

By using the hole 176 as a window, the collected light is split into two parts, each of which is subdivided in accordance with the teachings of the invention by suitable fresnelled prism deviators 120 and 178' similar to 94 in FIG. 2 and constructed according to methods disclosed in the aforesaid copending application Ser. No. 000,439. The deviator 120 will subdivide the back scattered light while the deviator 178' will subdivide forward scattered light which passes through the hole 176, this being generally the light that would normally have to be handled by the innermost rings of the element 120. Such light produces the beams 129, for example. This forward scattered light including beam 129 is collected and collimated by positioning collimating lens 181 so that its focal point is coincident with sensing zone or scattering point 126, producing substantially collimated light entering deviator 178'.

The multiple annular ray groups produced by deviator 178' are then focused by focusing lens 183 onto separate photodetectors, two of which are shown at 188 and 190. Thus, deviator 178' is positioned between collimating lens 181 and focusing lens 183 or other suitable focusing lens system.

The hole 176 permits the light which would otherwise be reflected at the smaller inner angles of the ellipsoid 122' to be magnified and makes it unnecessary to have extremely small rings on the fresnelled element 120 with corresponding small radial widths for such rings.

In coordinating and collating the data from the photodetectors, it is preferred that the data be processed in a computer. The rings for the elements 120 and the other fresnelled elements of the drawings preferably subtend equal angles as viewed from the sensing zone, but the computer may be programmed to compensate for rings of any varying width in the data being gathered. In FIG. 4 the rays of light which are shown are for deviator 120 intended to have each of the rings deviate an 11.25° increment; however, collimation allows large angular increments to be deviated and then focused without smearing.

It is noted that the intensity of the back scattered light which is achieved by the apparatus 1124' of FIG. 4 is normally substantially less than that of the forward scattered light. Instead of photodetectors of the conventional type, photomultipliers could be used with advantage although this will increase the overall cost of the apparatus. The number of such photomultipliers needed for good resolution is another important factor in cost. The utilization of the economical collimators and fresnel deviators provides advantages over known detecting systems, even with the use of expensive photomultipliers.

As an alternative to the array of separate photodetectors, a single vidicon or conventional television camera can be employed as shown in co-pending application Ser. No. 000,439. In addition, because different focusing lenses can be employed for independent focusing of different deviated ray groups, greater flexibility in photodetection equipment is made possible by this invention and combinations of different photodetectors are thereby facilitated.

Figure 5:
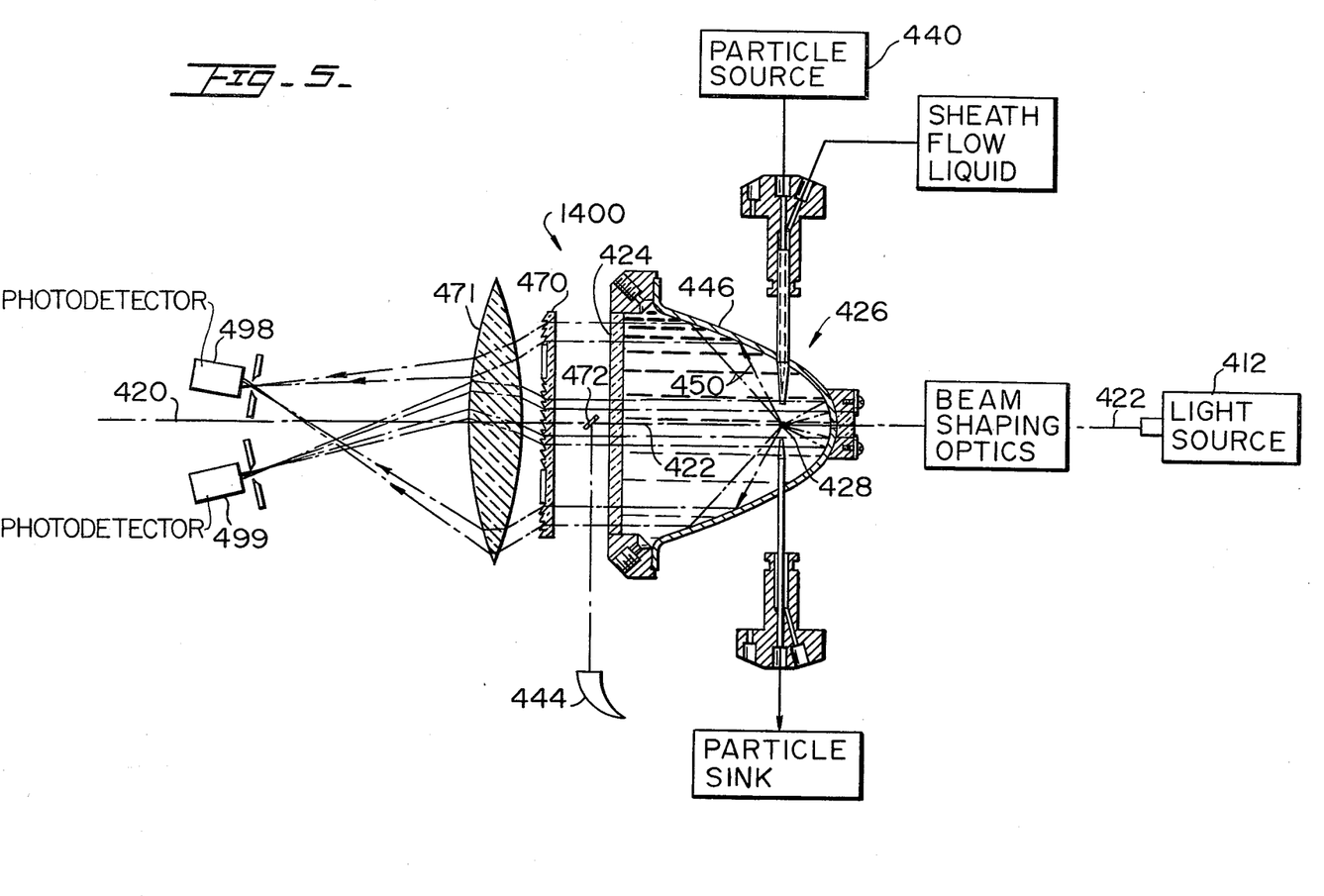
FIG. 5 is a diagrammatic generally sectional view through one embodiment of the invention in which a parabolic reflector both collects and collimates the radiant energy directed to a fresnel deviator.

An embodiment of this invention employing reflective collimation is illustrated in FIG. 5. This apparatus includes a flow cell 426 which has a parabolic reflector 446 equipped for sheath flow as shown with front opening closed off by a suitable closure 424 which is planar because the reradiated radiant energy which emerges from the reflector 446 emanates along lines which are parallel to the optical axis 420. The light source 412 in this instance is behind the reflector 446 as shown and it projects a beam of incident radiant energy along the path 422 toward the folding mirror 472 and onto the light dump 444, this beam of incident radiant energy passing through the sensing zone which coincides with the focal point 428 of the paraboloid 446. Particles originating at the source 440 move in sheath flow to the focal point 428 and at that point which comprises the sensing zone they intercept the beam 422 and reradiate some of the radiant energy of the beam. The rays from focal point 428 as for example rays 450, impinge the inner surface of the reflector 446 and are substantially collimated upon reflection projected parallel to the axis 420.

The collimated rays enter fresnel deviator 470 constructed in form similar to deviator 94 in FIG. 2. From deviator 470, the emerging deviated annular ray groups, having parallel rays within each group, enter focusing lens 471. Each ray group is focused onto a separate corresponding photodetector, such as photodetector 498 which registers the focused ray group originating as rays 450 from the sensing zone at focal point 428.

As in the other embodiments of this invention, focusing lens 471 or other suitable focusing lens system can be chosen for focal length independent of the other parameters of the apparatus. Parabolic reflector 446 provides a particular advantage in combining both collection and collimation of the reradiated energy into a single optical device; as a consequence, optical losses by refraction in lens collimation are eliminated.

As shown in FIG. 5, laser source is positioned to direct the incident beam to the sensing zone from the convex rear surface of the parabolic reflector; alternatively, the beam of incident radiation can be projected from the front opening of the parabolic reflector. When provided with a window similar to hole 176 in the ellipsoid of FIG. 4, back scattering and forward scattering with respect to the source of the beam can be separately measured without the collimating lens 119 employed in the embodiment of the invention shown in FIG. 4.

Because biological particle response can vary with different incident wavelengths, a combination of incident beams of different wavelength can be employed in the various embodiments of this invention with suitable modifications, for example, by using multiple lasers as more fully described in co-pending application Ser. No. 000,439.

It can be appreciated that the invention is capable of wide variation and flexibility of use both as to the apparatus and the method of using the same, without departing from the spirit or scope of the invention as defined in the appended claims.

What is desired to secure by Letters Patent of the United States is:

1. Apparatus for measuring the directional distribution of radiant energy reradiated from a particle for particle characterization which comprises:
   A. a source of radiant energy arranged to project an incident beam of radiant energy along a first axis,
   B. a sensing zone on said first axis,
   C. means for moving particles through said sensing zone to produce reradiation including scattering of the radiant energy from the beam,
   D. means for collecting a portion of said reradiated radiant energy,
   E. means for collimating at least a portion of the collected radiant energy,
   F. means for deviating the collimated radiant energy selectively with respect to different geometric portions of the collimated radiant energy,
   G. means for focusing the different deviated geometric portions of the collimated radiant energy at different respective locations, and
   H. means for measuring the intensity of the radiant energy focused at each location.

2. The apparatus as claimed in claim 1 wherein said collimating means comprises a collimating lens system.

3. The apparatus as claimed in claim 1 wherein said collecting means and said collimating means comprise a parabolic reflector defining a front opening and a convex rear surface and having its focal point coincident with the location of said sensing zone to provide collimated reflection of the reradiated radiant energy collected by said parabolic reflector.

4. The apparatus as claimed in claim 3 wherein said source projects the beam of incident radiant energy from the rear of the parabolic reflector to said sensing zone to provide information on reradiated energy primarily in the back directions with respect to said source.

5. The apparatus as claimed in claim 3 wherein said source projects the beam of incident radiant energy from the front of the parabolic reflector to said sensing zone to provide information of reradiated energy primarily in the forward directions with respect to said source.

6. The apparatus as claimed in claim 3 in which in addition to said first mentioned collecting and collimating means said parabolic reflector comprises an axial window in said rear surface and said apparatus further comprises second collimating means located with respect to said sensing zone to collimate scattered radiation from said window and second deviating means, second focusing means, and means for measuring the intensity of said scattered radiation.

7. The apparatus as claimed in claim 6 wherein said source projects the beam of incident radiant energy from the rear of the parabolic reflector to said sensing zone to provide information on reradiated energy from said window primarily in the back directions with respect to said source.

8. The apparatus as claimed in claim 6 wherein said source projects the beam of incident radiant energy from the front of the parabolic reflector to said sensing zone to provide information on reradiated energy from said window primarily in the forward directions with respect to said source.

9. The apparatus as claimed in claim 3 in which the particle moving means include means for entraining the particles in a first liquid and means for flowing the first liquid through the sensing zone.

10. The apparatus as claimed in claim 9 in which said parabolic reflector forms a closed vessel adapted to be filled with a second liquid whose index of refraction is substantially the same as that of the first liquid.

11. The apparatus as claimed in claim 10 in which means are provided for surrounding the first liquid with a third liquid of refractive index similar to that of the first and second liquids under pressure to cause the movement of the first liquid through the sensing zone to be a sheath flow.

12. The apparatus as claimed in claim 1 in which the deviating means comprises a lens composed of a plurality of prismatic components, each component being positioned to receive, transmit and deviate at an angle the radiant energy of a different one of said geometric portions in a different direction.

13. The apparatus as claimed in claim 12 in which all of said prismatic deviating components have the same angle of deviation.

14. The apparatus as claimed in claim 12 in which said lens is a fresnel lens and the components are integral with one another.

15. The apparatus as claimed in claim 1 in which said means for focusing comprises a focusing lens system.

16. Apparatus for measuring the scattering of radiant energy reradiated from particles for particle characterization which comprises:
   A. a source of radiant energy arranged to project a concentrated beam of said radiant energy along a first axis,
   B. a sensing zone, said concentrated beam being directed to pass through said sensing zone,
   C. means for moving particles in a stream of fluid to flow through said sensing zone at such an angle relative to said first axis and with such dilution in said fluid as to cause reradiation including scattering of radiant energy by each particle as it passes through said sensing zone,
   D. means for collecting at least a portion of said scattered radiant energy from certain scattering angles about said sensing zone and projecting same as a composite cone of varying intensity considered on a planar frontal aspect, the variations in intensity being related generally to the respective certain scattering angles, said composite cone being projected toward a focusing point in space on said first axis remote from said sensing zone,
   E. means for collimating the composite cone of radiant energy to project a pattern of parallel rays of radiant energy therefrom,
   F. deviating means including a plurality of deviating components each constructed and arranged to separate different geometric portions of the pattern of parallel rays into plural, different ray groups deviated along an equivalent plural number of different respective paths, each path having a different direction divergent from said axis, G. means for focusing said different deviated ray groups to cause confluence of said ray groups at corresponding different locations, and H. photoresponsive means positioned at said locations producing a separate signal for each location related respectively to the intensity of radiant energy confluenced at said locations.

17. The apparatus as claimed in claim 16 in which said collecting means comprises an ellipsoidal reflector having a forward opening closed by a spherical transparent closure wherein said sensing zone is located on the interior, minor focal point of said ellipsoidal reflector whereby a converging focal point is located on the exterior of said ellipsoidal reflector.

18. The apparatus as claimed in claim 17 wherein said collimating means comprises a collimating lens system.

19. The apparatus as claimed in claim 18 wherein said collimating lens system comprises a negative lens positioned to have its focal point coincident with the exterior focal point of said ellipsoidal reflector, for collimation of reflected reradiation from said ellipsoidal reflector.

20. The apparatus as claimed in claim 18 in which in addition to said first mentioned collecting means said elliptical reflector comprises an axial window at the closed end and said apparatus further comprises second collimating means located with respect to said sensing zone to collimate scattered radiation from said window, and second deviating means, second focusing means, and means for measuring the intensity of said scattered radiation.

21. The apparatus as claimed in claim 18 in which the fluid of said moving means comprises a first liquid entraining the particles through the sensing zone.

22. The apparatus as claimed in claim 21 in which said ellipsoidal reflector forms a closed vessel adapted to be filled with a second liquid whose index of refraction is substantially the same as that of the first liquid.

23. The apparatus as claimed in claim 22 in which means are provided for surrounding the first liquid with a third liquid of refractive index similar to that of the first and second liquids under pressure to cause the movement of the first liquid through the sensing zone to be a sheath flow.

24. The apparatus as claimed in claim 16 in which the deviating means comprise a lens and the deviating components are prismatic, each component being positioned to receive, transmit and deviate at an angle the radiant energy of a different one of said ray groups.

25. The apparatus as claimed in claim 24 in which all of said prismatic deviating components have the same angle of deviation.

26. The apparatus as claimed in claim 24 in which said lens is a fresnel lens and the components are integral with one another.

27. The apparatus as claimed in claim 16 in which said means for focusing comprises a focusing lens system.

28. A method of measuring the directional distribution properties of the radiant energy reradiated from a particle for particle characterization which comprises:

A. passing the particle through a sensing zone and illuminating the particle with an incident beam of radiant energy, B. collecting at least some of the directionally distributed radiant energy produced by the intersection of the particle and the beam, C. collimating at least a portion of the collected radiant energy, D. deviating the collimated radiant energy along a plurality of different paths independently of the collecting,
  i. each path being arranged to comprise the radiant energy gathered from a particular geometric area of the collimated radiant energy,
  ii. the geometric areas being different, E. focusing the deviated radiant energy in each said different path at corresponding different locations spaced from one another, and F. measuring the respective intensities of the radiant energy focused at the different locations.

29. The method as claimed in claim 28 wherein the directionally distributed radiant energy collected and collimated comprises primarily forward scattered reradiation with respect to said incident beam.

30. The method as claimed in claim 28 wherein the directionally distributed radiant energy collected and collimated comprises both back scattered and forward scattered reradiation with respect to said incident beam.

31. The method as claimed in claim 28 wherein at least a portion of the collected directionally distributed radiant energy is collimated by reflection.

32. The method as claimed in claim 28 wherein at least a portion of the collected directionally distributed radiant energy is collimated by refraction.

* * * * *